United States Patent [19]

Audiau et al.

[11] Patent Number: 5,049,574
[45] Date of Patent: Sep. 17, 1991

[54] 5-TRIFLUORMETHOXY-2-BEN-ZIMIDAZOLAMINE COMPOUNDS

[75] Inventors: Francois Audiau, Charenton Le Pont; Christian Renault, Taverny, both of France

[73] Assignee: Rhone-Poulenc Sante, Antony, France

[21] Appl. No.: 481,063

[22] Filed: Feb. 16, 1990

[30] Foreign Application Priority Data

Feb. 20, 1989 [FR] France .................................. 89 02168

[51] Int. Cl.$^5$ .................. C07D 235/30; A61K 31/415
[52] U.S. Cl. ...................................... 514/395; 548/239
[58] Field of Search ......................... 548/329; 514/395

[56] References Cited

U.S. PATENT DOCUMENTS

| | | | |
|---|---|---|---|
| 3,309,987 | 9/1968 | Woods et al. | 548/329 |
| 4,536,502 | 8/1985 | Giraudon et al. | 548/329 |
| 4,593,105 | 6/1986 | Gencarelli et al. | 548/329 |

FOREIGN PATENT DOCUMENTS

| | | | |
|---|---|---|---|
| 0080555 | 6/1983 | European Pat. Off. | 548/329 |
| 3013277 | 10/1981 | Fed. Rep. of Germany | 548/329 |

OTHER PUBLICATIONS

Elderfield, Heterocyclic Compounds, 5, 285, (1957).
The Role of Glutamate in Neurotransmission and in Neurologic Disease, Neurological Review, vol. 43, pp. 1058–1063, Oct. 1986.
Blockade of N-Methyl-D-Aspartate Receptors May Protect Against Ischemic Damage in the Brain, Simon, et al., Science, vol. 26, pp. 851–852, Aug. 1984.
L-Glutamate, excitatory amino acid receptors and brain function, Graham E. Fagg, TINS, May 1985, pp. 207–209.
Excitatory Amino Acid Receptors in the Vertebrate Central Nervous System, Collingridge, et al., Pharmacological Reviews, vol. 40, No. 2, pp. 143–145, 193–195.
Frontal Cortical and Left Temporal Glutamatergic Dysfunction in Schizophrenia, Deakin, et al., J. Neurochem. 52, 1781–1786 (1989).
Changes in extracellular amino acid neurotransmitters produced by focal cerebral ischemia, Graham et al., Neuroscience Letters 110 (1990), 124–130.

*Primary Examiner*—Alan L. Rotman
*Assistant Examiner*—Zinna Northington-Davis
*Attorney, Agent, or Firm*—Morgan & Finnegan

[57] ABSTRACT

5-Trifluoromethoxy-2-benzimidazolamine and its salts with an inorganic or organic acid, its preparation and medicinal products containing it.

4 Claims, No Drawings

5-TRIFLUORMETHOXY-2-BENZIMIDAZOLAMINE COMPOUNDS

DETAILED DESCRIPTION OF THE INVENTION

The present invention relates to 5-trifluoromethoxy-2-benzimidazolamine, to its preparation and to medicinal products containing it.

5-Trifluoromethoxy-2-benzimidazolamine is represented by the formula

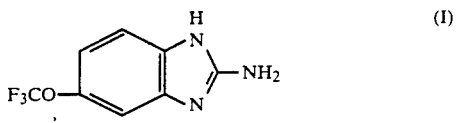

The salts of the compound of formula (I) with inorganic or organic acids also form part of the invention.

The compound of the formula (I) may be prepared by the action of cyanogen bromide on 4-trifluoromethoxy-1,2-benzenediamine.

This process consists of an adaptation of the method described by R. C. ELDERFIELD, Heterocyclic Compounds, 1957, 5, 285 for the preparation of 2-benzimidazolamine.

The reaction of cyanogen bromide with 4-trifluoromethoxy-1,2-benzenediamine may be performed at about 0° C. in an inert aqueous-organic medium. As an organic solvent, tetrachloroethane may be used.

The cyanogen bromide may be generated in situ by the action of bromine on sodium cyanide according to the method described in Organic Synthesis, 1983, 61, 35.

The reaction mixture obtained is treated according to conventional physical methods (extraction, crystallization, chromatography) or chemical methods (salt formation and regeneration of the base) in order to isolate the compound of formula (I) in the pure state.

The compound of formula (I) in free base form ma be optionally converted to an addition salt with an inorganic or organic acid by the action of such an acid in an inert organic solvent such as an alcohol, a ketone, an ether or a chlorinated solvent.

The compound of formula (I) and its salts possess advantageous pharmacological properties. This compound is an aspartic acid antagonist, and is active with respect to the electrophysiological responses induced in rats by the iontophoretic application of neuroexcitatory amino acids, in particular kainic acid. This compound is hence useful for the treatment of neurological and psychiatric disorders, especially psychotic states (schizophrenia), epilepsy, neurodegenerative diseases such as Alzheimer's disease or Huntington's disease and cerebral ischaemia The antagonist properties with respect to aspartic acid were determined by measuring the inhibition of the increase in the cyclic guanosine monophosphate (GMP) level induced by aspartic acid according to the method of J. GARTHWAITE, Neuroscience, 1982, 7, 2491–2497.

Young male rats (8–12 days) are decapitated and the cerebellum is rapidly removed and placed in buffer at 0° C. (122 mM NaCl, 3 mM KCl, 1.2 mM $MgSO_4$, 1.3 mM $CaCl_2$, 0.4 mM $KH_2PO_4$, 25 mM $NaHCO_3$ and 10 mM glucose, containing 0.5 mM theophylline to avoid enzymatic degradation of the cyclic GMP). Cerebellum slices (0.6–0.8 mm) are incubated for 40 min at 37° C. under a 95% $O_2$/5% $CO_2$ atmosphere in the same buffer (20 cc), then washed and placed again in buffer (15 cc) under the same conditions for 60 min.

The slices are washed again and transferred to buffer (15 cc) containing the test products After incubation for 18 min, the tissues are ground in ethanol (2 cc) and the cyclic GMP level is determined by radioimmunoassay according to a method described by A. L. STEINER, C. W. PARKER and D. M. KIPNIS. J. Biol. Chem. 1972, 247, 1106.

Aspartic acid is used at a concentration of 100 μm, and the test product is added 3 min before the aspartic acid at a concentration of 25, 50 or 100 μM. The results used are the mean of 5 to 10 experiments for each concentration, and an $IC_{50}$, which is the concentration inhibiting by 50% the increase in the cyclic GMP level induced by aspartic acid, is determined.

The compound of formula (I) has an $IC_{50}$ of 30 μM in this test.

The activity with respect to the electrophysiological responses induced in rats by the iontophoretic application of neuroexcitatory amino acids, such as N-methyl-D-aspartic acid (NMDA), kainic acid and quisqualic acid (QI), is determined according to the method of M. R. MARTIN et al., European Journal of Pharmacology, 1977, Vol. 42, 291–298.

At a dose of 1 mg/kg, the compound of formula (I) induces, 30 minutes after its administration, a decrease of 90% in the electrophysiological responses to kainate and of 20% in the responses to NMDA and to QI.

The compound according to the invention and its salts possess low toxicity. The $LD_{50}$ of the compound of Example 1 is 620 mg/kg when administered orally to mice. This $LD_{50}$ was calculated after 3 days of observation by the cumulative method of J. J. REED and H. MUENCH, Amer. J. Hyg., 1938, 27, 493.

For medicinal use, the product of formula (I) may be employed as it is or in the state of a salt with a pharmaceutically acceptable acid.

As pharmaceutically acceptable salts, there may be mentioned the addition salts with an inorganic acid, such as the hydrochloride, sulphate, nitrate or phosphate, or with an organic acid, such as the acetate, propionate, succinate, benzoate, fumarate, theophylline acetate, salicylate, methylenebis(2-hydroxynaphthoate) or substitution derivatives of these products.

EXAMPLES

The invention will now be described in connection with nonlimiting examples.

EXAMPLE 1

Sodium cyanide (1.79 9), dissolved in water (5.6 cc) is added dropwise to a mixture, cooled to 0° C., of bromine (5.8 9) and water (5.6 cc). After 1 hour's contact at 0° C., a solution of 4-trifluoromethoxy-1,2-benzenediamine (7 g) in tetrachloroethane (7 cc) is added dropwise. After 2 hours at 0° C., the reaction mixture is poured into water (500 cc). Dichloromethane (500 cc) is added and the mixture is stirred for 20 minutes. After settling has taken place, the aqueous phase is separated and washed with dichloromethane (2×150 cc) and alkalinized to pH 8 with sodium carbonate. The base is extracted with ethyl acetate (3×300 cc) and the organic phase is dried over magnesium sulphate and evaporated under reduced pressure. Crude base (9.5 g) is obtained, which is purified by preparative HPLC using a dichloromethane/ethanol mixture (95:5 by volume) as eluent. An oil is recovered, which is converted to a hydrochloride in ethyl ether. 5-Trifluoromethoxy-2-benzimidazolamine hydrochloride (4.8 g), m.p. 180° C., is obtained.

4-Trifluoromethoxy-1,2-benzenediamine is prepared according to Zhur. Obshchei. Khim., 1961, 31, 915.

The medicinal products according to the invention consist of the compound of formula (I) or a salt of this compound, in the pure state or in the form of a composition in which it is combined with any other pharmaceutically compatible product, which can be inert or physiologically active. The medicinal products according to the invention may be used orally, parenterally, rectally or topically.

As solid compositions for oral administration, tablets, pills, powders (gelatin capsules, wafer capsules) or granules may be used. In these compositions, the active principle according to the invention is mixed with one or more inert diluents such as starch, cellulose, sucrose, lactose or silica. These compositions can also comprise substances other than diluents, e.g. one or more lubricants such as magnesium stearate or talc, a coloring, a coating (dragées) or a varnish.

As liquid compositions for oral administration, solutions, suspensions, emulsions, syrups and elixirs of a pharmaceutically acceptable nature, containing inert diluents such as water, ethanol, glycerol, vegetable oils or liquid paraffin, may be used. These compositions can comprise substances other than diluents, e.g. wetting products, sweeteners, thickeners, flavorings or stabilizers.

The sterile compositions for parenteral administration can preferably be solutions, aqueous or otherwise, suspensions or emulsions. As a solvent or vehicle, water, propylene glycol, a polyethylene glycol, vegetable oils, especially olive oil, injectable organic esters, e.g. ethyl oleate or other suitable organic solvents may be employed These compositions can also contain adjuvants, especially wetting agents, tonicity regulators, emulsifiers, dispersants and stabilizers. The sterilization may be carried out in several ways, e.g. by aseptic filtration, by incorporating sterilizing agents in the composition, by irradiation or by heating. They may also be prepared in the form of sterile solid compositions which can be dissolved at the time of use in a sterile injectable medium.

The compositions for rectal administration are suppositories or rectal capsules, which contain, apart from the active product, excipients such as cocoa butter, semi-synthetic glycerides or polyethylene glycols.

The compositions for topical administration can be, e.g., creams, ointments, lotions, eye washes, mouth washes, nasal drops or aerosols In human therapy, the compound according to the invention is especially useful for the treatment of neurological and psychiatric disorders, especially psychotic states (schizophrenia), epilepsy, neurodegenerative diseases such as Alzheimer's disease or Huntington's disease and cerebral ischaemia The doses depend on the effect sought, the treatment period and the administration route used; they are generally between 50 and 500 mg per day in oral administration for an adult, with unit doses ranging from 10 to 50 mg of active substance.

Generally speaking, the doctor will determine the appropriate dosage in accordance with the age and weight and all factors characteristic of the subject to be treated.

The examples which follow illustrate compositions according to the invention:

EXAMPLE A

Hard gelatin capsules containing 25 mg of active product and having the following composition are prepared according to the usual technique:

| | |
|---|---|
| 5-Trifluromethoxy-2-benzimidazolamine | 25 mg |
| Microcrystalline cellulose | 75 mg |
| Mannitol | 41 mg |
| Colloidal silica | 4 mg |
| Carboxymethyl starch sodium | 25 mg |
| Talc | 18 mg |
| Magnesium stearate | 2 mg |
| Polyvidone excipient | 10 mg |

EXAMPLE B

Tablets containing 50 mg of active product and having the following composition are prepared according to the usual technique:

| | |
|---|---|
| 5-Trifluoromethoxy-2-benzimidazolamine | 50 mg |
| Microcrystalline cellulose | 75 mg |
| Mannitol | 41 mg |
| Polyvidone excipient | 10 mg |
| Carboxymethyl starch | 25 mg |
| Colloidal silica | 4 mg |
| Talc | 18 mg |
| Magnesium stearate | 2 mg |

EXAMPLE C

An injectable solution containing 10 mg of active product and having the following composition is prepared:

| | |
|---|---|
| 5-Trifluoromethoxy-2-benzimidazolamine | 10 mg |
| Benzoic acid | 80 mg |
| Benzyl alcohol | 0.06 cc |
| Sodium benzoate | 80 mg |
| Ethanol, 95% | 0.4 cc |
| Sodium hydroxide | 24 mg |
| Propylene glycol | 1.6 cc |
| Water q.s. | 4 cc |

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

We claim:

1. 5-Trifluoromethyoxy-2-benzimidazolamine or its salts with an inorganic or organic acid.

2. A pharmaceutical composition useful for the treatment of a medicinal condition associated with the effects of neuroexcitatory amino acids comprising, as active principle, an effective amount of 5-trifluoromethoxy-2-benzimidazolamine or one of its pharmaceutically acceptable salts with an inorganic or organic acid, in association with at least one compatible and pharmaceutically acceptable adjuvant or diluent.

3. A pharmaceutical composition according to claim 2 for the treatment of psychotic diseases including schizophrenia, epilepsy, neurodegenerative diseases including Alzheimer's disease or Huntington's disease and cerebral ischaemia.

4. A method for the treatment of a medical condition associated with effects of neuroexcitatory amino acids which comprises administering to a subject in need of such treatment an amount of 5-trifluoromethoxy-2-benzimidazolamine or one of its pharmaceutically acceptable salts with an inorganic or organic acid sufficient to inhibit such effects.

* * * * *